United States Patent [19]

Goldhaber

[11] 4,396,382
[45] Aug. 2, 1983

[54] MULTIPLE CHAMBER SYSTEM FOR PERITONEAL DIALYSIS

[75] Inventor: Richard P. Goldhaber, Genese, Belgium

[73] Assignee: Travenol European Research and Development Centre, Brussels, Belgium

[21] Appl. No.: 327,982

[22] Filed: Dec. 7, 1981

[51] Int. Cl.³ .............................. A61J 7/00; A61J 1/00
[52] U.S. Cl. ....................................... 604/28; 604/410; 604/29
[58] Field of Search .......... 128/213 A, 214 R, 214 D, 128/DIG. 24, 272; 222/94, 95, 105; 150/1, 2.5; 604/29, 410

[56] References Cited

U.S. PATENT DOCUMENTS

| | | | |
|---|---|---|---|
| 3,228,395 | 1/1966 | Gewecke | 128/214 F |
| 3,620,215 | 11/1971 | Tusk et al. | 128/213 A |
| 3,943,929 | 3/1976 | Patel | 128/DIG. 24 X |
| 4,239,041 | 12/1980 | Popovich et al. | 604/28 X |
| 4,270,533 | 6/1981 | Andreas | 128/214 D X |
| 4,282,863 | 8/1981 | Beigler et al. | 128/214 D |
| 4,326,526 | 4/1982 | Buck et al. | 128/213 A |

FOREIGN PATENT DOCUMENTS 2455462  11/1980  France .

Primary Examiner—Stephen C. Pellegrino
Attorney, Agent, or Firm—Garrettson Ellis; Paul C. Flattery

[57] ABSTRACT

A solution bag formed of three plastic walls sealed together about their peripheries to define a pair of separate chambers is provided for peritoneal dialysis and the like.

14 Claims, 6 Drawing Figures

MULTIPLE CHAMBER SYSTEM FOR PERITONEAL DIALYSIS

TECHNICAL FIELD

Peritoneal dialysis, particularly in the form of continuous ambulatory peritoneal dialysis, disclosed in U.S. Pat. No. 4,239,041, is a rapidly growing technique for the maintenance of patients who have lost kidney function. The technique exhibits great convenience of use compared with more conventional dialysis, because the patient can be free to move about during the entire day, while undergoing continuous diffusion exchange with peritoneal dialysis solution in the peritoneal cavity. Also, peritoneal dialysis procedures tend to be considerably less expensive than hemodialysis procedures.

It is considered desirable by some experts to pass the fresh peritoneal dialysis solution through a bacteria blocking filter immediately prior to entry of the solution into the peritoneal cavity. However, as a problem with this technique, it has been found that after the peritoneal dialysis solution has resided in the peritoneum for a period of time, if it comes into contact with the filter it tends to quickly clog the filter, to interfere with further use thereof.

In some forms of peritoneal dialysis the filter can remain on the part of the peritoneal tube which communicates with the peritoneal catheter, being worn by the patient for a substantial length of time, i.e., several weeks. Thus, in the event that the peritoneal dialysis solution comes into contact with the filter after having resided in the peritoneal cavity, the filter can become obstructed prior to the expiration of the intended period of use.

By this invention, a structure is disclosed in which the filter can be protected from contact with spent peritoneal dialysis solution, while at the same time a single bag may be used both to provide the solution to the peritoneal cavity, and also to receive spent solution from the peritoneal cavity, without coming into contact with the filter to clog it.

Also, the same bag may be used to advantage in peritoneal dialysis without a filter, when the bag is removed between exchanges, to reduce the incidence of peritonitis by reducing the required number of connections made.

DESCRIPTION OF PRIOR ART

French published Patent Application 2,455,462 (SMAD) discloses apparatus for peritoneal dialysis, for conveying dialysis solution between the peritoneal cavity and a container. The apparatus defines a first passageway which contains a filter, and a second bypass passageway which bypasses the filter so that dialysis solution from the peritoneal cavity can pass back to the container without contact with the filter. However, it has been found that even a small amount of the spent peritoneal dialysis solution, entering into contact with the filter, can degrade its capability to function. Those few drops of solution can reside in the upstream portion of the set as the spent solution flows from the peritoneal cavity, so that the next aliquot of fresh peritoneal dialysis solution passing through the set and filter can carry the few drops of spent peritoneal dialysis solution through the filter, with the result that over a period of use the filter is degraded in its functioning.

By this invention, spent peritoneal dialysis solution can be completely kept away from the filter despite its passage through the same tubular set back to a container, so that not even one drop of spent peritoneal dialysis solution comes into contact with the filter. Additionally, with this invention, fewer and safer connections can be made per peritoneal dialysis procedure.

DESCRIPTION OF THE INVENTION

In accordance with this invention a solution delivery system for peritoneal dialysis may include the following.

A peritoneal tube is provided for flow communication to the peritoneal cavity of a patient, being typically attached to a peritoneal catheter through one end thereof. The tube carries a branched pair of tubular arms at its other end, one of the arms carrying a dialysis solution filter in flow communication therewith.

A solution bag defining separate chambers and preferably formed of three plastic walls, sealed together about their peripheries to define a pair of separate chambers, is provided. Port tubes communicate with each of the chambers. One of the chambers is filled with dialysis solution and the other is empty, with the port tube of the one chamber connecting with the tubular arm which carries the filter, and the port tube of the empty chamber connecting with the other tubular arm. Flow regulating means such as slide or other clamps are provided to control flow through the tubular arms.

As the result of this, fresh dialysis solution from the one chamber may pass from the chamber through the filter and peritoneal tube into the peritoneal cavity. The spent dialysis solution may pass from the peritoneal tube through the other tubular arm into the other chamber without entering into contact with the filter.

Since the spent peritoneal dialysis solution resides in the other chamber, there is no way that even a few drops can recycle into the port tube which is connected with the tubular arm which carries the filter. Thus the upstream portion of such filter-carrying port tube remains completely free of spent peritoneal dialysis solution. The downstream portion of the port tube which carries the filter may be sealed with the flow regulating means during the process.

Following this, the bag of solution may be disconnected and disposed of, and a fresh bag of solution reconnected. Once again, the port tube of the bag communicating with the chamber filled with fresh dialysis solution communicates with the tubular arm that carries the filter. Thus, when opened, fresh dialysis solution passes through the filter and washes any spent peritoneal dialysis solution in the lower end of that tubular arm into the peritoneal cavity. Thus the filter is completely protected from contact with spent peritoneal dialysis solution, making use of the double chamber bag and the branching connections of this invention.

As a further advantage of this structure, any bacteria that are collected on the upstream side of the filter are completely isolated from the peritoneal cavity, despite the fact that the double chamber bag of this invention has another entry port for receiving spent peritoneal dialysis solution. There is no communication between the two entry ports of the bag since they lead to separate chambers. To the contrary, in the event that a bypass system is used so that the spent peritoneal dialysis solution may bypass the filter and be drained back into the same bag from which the fresh solution was obtained, it is possible for bacteria retained on the upstream side of the filter to migrate from the bag through the shunt tube, bypassing the filter to enter the peritoneal cavity.

Alternatively, the invention of this application may be used in a system which does not carry a filter. A solution bag formed of three plastic walls, having its port tubes communicating with each of the chambers, may have port tubes that join together to a single tube, terminated at its end by a single connector which is adapted to connect with the peritoneal tube for flow communication to the peritoneal cavity of the patient. Flow control means may be provided for each of the port tubes, for example, a slide clamp in the case of the port tube communicating with the empty bag chamber, and an internal breakaway member in the case of the port tube which communicates with the chamber of the bag which is filled with fresh peritoneal dialysis solution.

Accordingly, the bag may be connected to the peritoneal tube of the patient through the connector when the patient is ready for an exchange of dialysis solution. The slide clamp may be opened, and the spent peritoneal dialysis solution may flow from the peritoneal cavity of the patient into the empty chamber of the bag, the bag being proportioned so that it is capable of carrying the spent peritoneal dialysis solution in one bag chamber, while the fresh peritoneal dialysis solution resides in the other bag chamber.

Following this, the slide clamp closes off the port tube that communicates with the formerly empty chamber of the bag, and the flow control means of the other port tube is opened, permitting the fresh peritoneal dialysis solution to flow into the patient's peritoneal cavity. By this means, a single bag can be used, with a single connection made to the peritoneal tube, to both receive the spent peritoneal dialysis solution and to provide the fresh peritoneal dialysis solution.

After the fresh peritoneal dialysis solution has been administered, the bag may be disconnected; the end of the peritoneal tube capped with a bacteria-proof closure; and the patient can resume his normal activities without having to carry the flattened bag. Furthermore, this advantage can be achieved with only a single connection made between a bag and the peritoneal tube per replacement of peritoneal dialysis solution.

Other uses which can be made of the double compartment container of this invention are for the storage of two incompatible solutions which can be mixed together immediately before use, for example bicarbonate-stabilized dialysis solution, where the bicarbonate solution is separately stored from the dialysis solution and added immediately before or during the administration process.

In other fields, one of the compartments of the two-compartment bag may hold an amino acid solution, and the other compartment may contain glucose or other source of carbohydrate nutrition, optionally with saline and other electrolytes, for the purpose of dialysis or total parenteral nutrition.

DESCRIPTION OF SPECIFIC EMBODIMENTS

Figure 1:
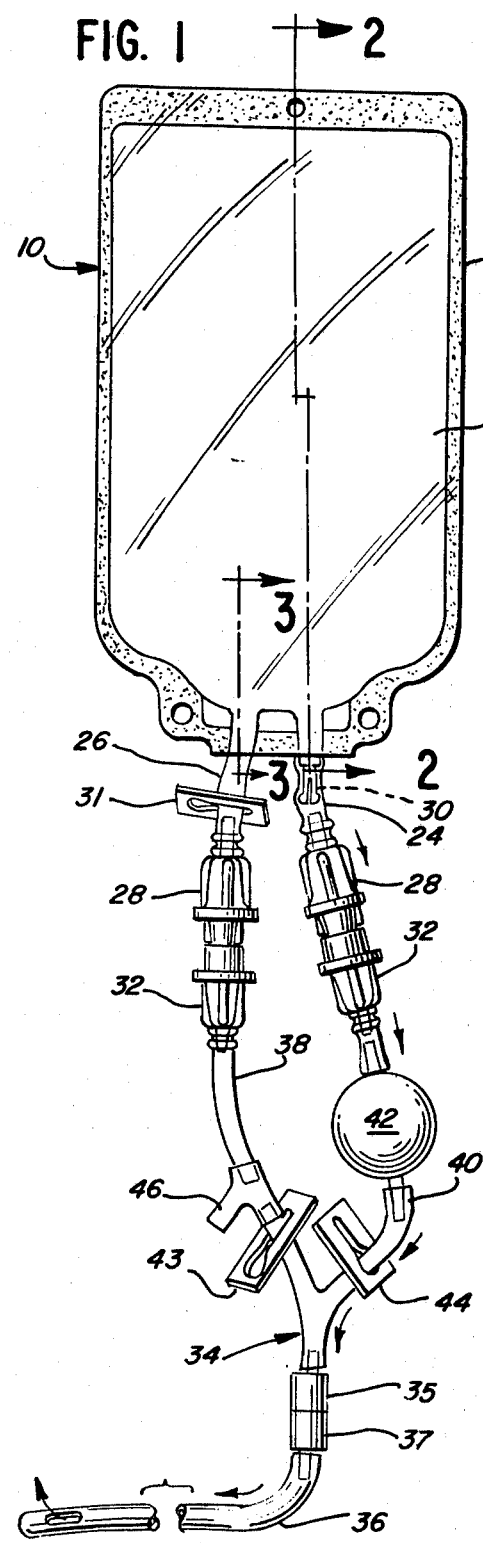
FIG. 1 is an elevational viw of a solution bag of this invention, connected to a filter-carrying peritoneal set which, in turn, communicates with the implanted peritoneal dialysis catheter in a patient.
Figure 2:
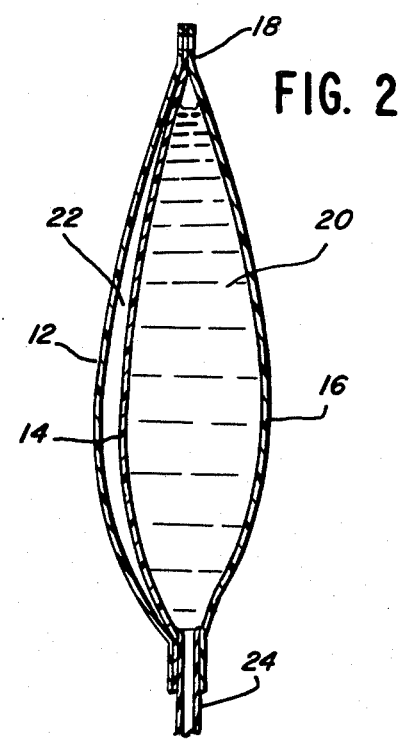
FIG. 2 is a sectional view taken along line 2—2 of FIG. 1.
Figure 3:
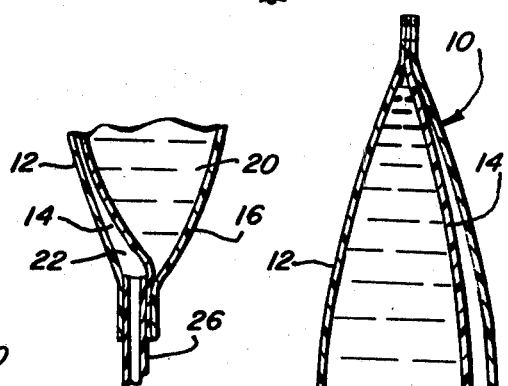
FIG. 3 is a fragmentary sectional view taken along line 3—3 of FIG. 1.

Referring to FIGS. 1-3, solution bag 10 is disclosed, being formed of three flexible plastic walls 12, 14, 16 sealed together about their peripheries 18 to define a pair of separate chambers 20, 22. The construction of bag 10 can be similar to the construction of presently sold polyvinyl chloride blood and solution bags, with the exception that three plastic walls are sealed about their peripheries rather than the customary two plastic walls, the result being that separate chambers 20, 22 are defined.

Port tubes 24, 26 are also provided, with port tube 24 communicating with chamber 20, and port tube 26 communicating with chamber 22. This is simply accomplished by inserting the port tubes, prior to sealing of periphery 18, in such a manner that they project into the bag on opposite sides of inner wall 14, followed by customary heat sealing of the periphery 18 so that the port tubes 24, 26 are positioned through the heat seal in accordance with customary technology.

Each of port tubes 24, 26 are terminated by connectors 28 which may be of a design, for example, as shown in U.S. Pat. No. 4,294,250.

Frangible, internal breakaway seal member 30 may be provided in the interior of port tube 24, for sealing of chamber 20 until access is desired. While any desired design of seal member 30 may be used, one particularly preferred design is as disclosed in U.S. application Ser. No. 086,102, filed Oct. 18, 1979, and entitled "Breakaway Valve". Such a seal may also be used for port tube 26 also, if desired, but slide clamp 31 is specifically shown for flow control through port tube 26.

Compartment 20 may be filled with fresh peritoneal dialysis solution in this particular embodiment, while compartment 22 is initially empty, so that inner wall 14 rests against outer wall 12 of the container along much of its extent. In the drawings, however, inner wall 14 is shown spaced from the outer walls for clarity of disclosure.

Connectors 28 of bag 10 are, in turn, connected with a pair of mating connectors 32 of a peritoneal tube 34 which typically may be a peritoneal set terminating with conventional connector means 35, attachable to a connector 37 of peritoneal catheter 36 implanted in a patient. Connector 37 may be a conventional titanium connector positioned on the end of catheter 36, while connector means 35 may be a double seal plastic connector. This connector system 35, 37 is presently sold for continuous ambulatory peritoneal dialysis by Travenol Laboratories, Inc. of Deerfield, Illinois.

Connectors 32 may be the mating connectors to connectors 28, of the design disclosed in U.S. Pat. No. 4,294,250.

Peritoneal set 34 defines a pair of branched tubular arms 38, 40, one of which carries a filter 42, typically a 0.22 micron hydrophobic bacteria filter.

Slide clamps 43, 44 (or other clamps or valves as desired) are also provided on arms 38, 40 to selectively control the flow therethrough. Conventional Y site 46 may optionally be provided in tubular arm 38 for the application of antiseptic, while clamp 43 is closed, to sterilize the connection between connectors 28, 32 before opening clamp 43 for outflow of spent dialysis solution.

It should be noted that the term "sterile" as used herein also includes the concept of substantial sterility, in which the population of microorganisms has been reduced to such a level that they do not cause the patient to exhibit significant symptoms of infection.

For use of the structure of FIGS. 1-4, the connection is made between port tubes 24, 26 and tubular arms 38, 40. The patient typically carries tubular set 34 in connection with the peritoneal catheter 36 for a substantial length of time, perhaps a month, with bag 10 being switched with every peritoneal dialysis procedure.

Bag 10 is thus connected, making use of a sterile procedure to avoid contamination of connectors 28, 32, and optionally making use of a sterilizing procedure with ultraviolet radiation or another sterilizing agent.

After the sterile connection has been made, the breakaway seal 30 in port tube 24 is opened, with clamp 44 being open and clamp 43 being closed, to permit the fresh peritoneal dialysis solution in chamber 20 to flow through filter disc 42 and through catheter 36 into the peritoneal cavity, to prevent any contamination passing into the peritoneal cavity.

This, of course, presupposes that any peritoneal dialysis solution previously in the peritoneal cavity has been already removed.

In the alternative, it may be desired for the patient to proceed through a dwell period in which the peritoneal dialysis solution resides in the peritoneal cavity with tubular set 34 being unconnected to a bag. In that instance, bag 10 may then be connected in sterile manner between the respective connectors 28, 32, and, as a first step, slide clamps 31 and 43 may be opened, with clamp 44 being closed, and the spent peritoneal dialysis solution is drained through set 34 and port tube 26, to fill bag chamber 22 prior to draining chamber 20 of its fresh dialysis solution. In this event, bag 10, of course, must be proportioned to simultaneously hold both the fresh and the spent peritoneal dialysis solution.

After removal of the spent peritoneal dialysis solution from the peritoneal cavity, whether drained into the present bag, or previously drained into another bag prior to connection of bag 10, the fresh dialysis solution is passed through tubular port 24, filter disc 42, and catheter 36 into the peritoneal cavity.

Thereafter, if bag 10 is completely empty it may be worn by the patent without disconnection during the dwell period in which the solution resides in the peritoneal cavity, and then used to receive spent dialysis solution. Alternatively, it may be disconnected, with connectors 32 being capped with sealing caps.

Figure 4:
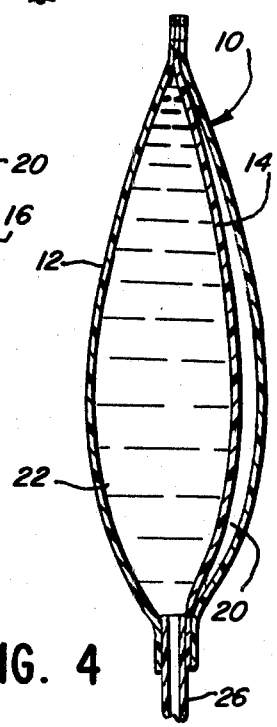
FIG. 4 is a sectional view similar to that of FIG. 3, but showing the chamber filled with liquid in FIG. 3 as being empty, and the empty chamber as shown in FIG. 3 being filled with liquid.

FIG. 4 shows bag 10 after the fresh dialysis solution has been drained from chamber 20 and the spent dialysis solution has passed into chamber 22, immediately prior to disconnection thereof from connectors 32. It can be seen that inner wall 14 has moved to the other side of the bag, to be generally in contact with outer bag wall 16.

A major advantage of this procedure is that, when properly performed, no spent peritoneal dialysis solution can get into contact with filter 42 to degrade its performance. Thus filter 42 can be repeatedly used for a substantial length of time, providing increased assurance of sterile conditions, since any contamination which might come from the peritoneal dialysis solution or from the connection of connector 32 will be retained by filter 42. A filter is less necessary on tubular arm 38, because that tubular arm only receives outflowing, spent peritoneal dialysis solution rather than inflowing solution. Clamp 44 prevents any upstream migration of the spent peritoneal dialysis solution into tubular arm 40, while the double chamber characteristic of bag 10 prevents any migration of spent peritoneal dialysis solution into tubular arm 24, to be driven through filter 42 upon the next administration of fresh dialysis solution.

Figure 5:
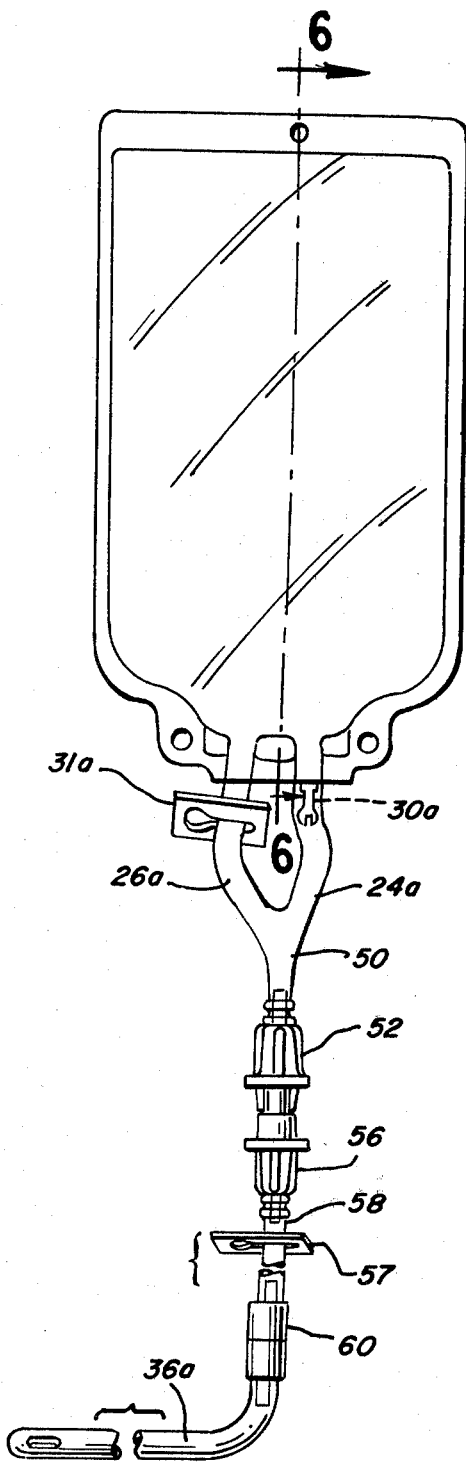
FIG. 5 is an elevational view of another embodiment of the system of this invention utilizing a double chamber bag, shown connected to a peritoneal set which, in turn, connects to an implanted catheter in the peritoneal cavity of the patient.
Figure 6:
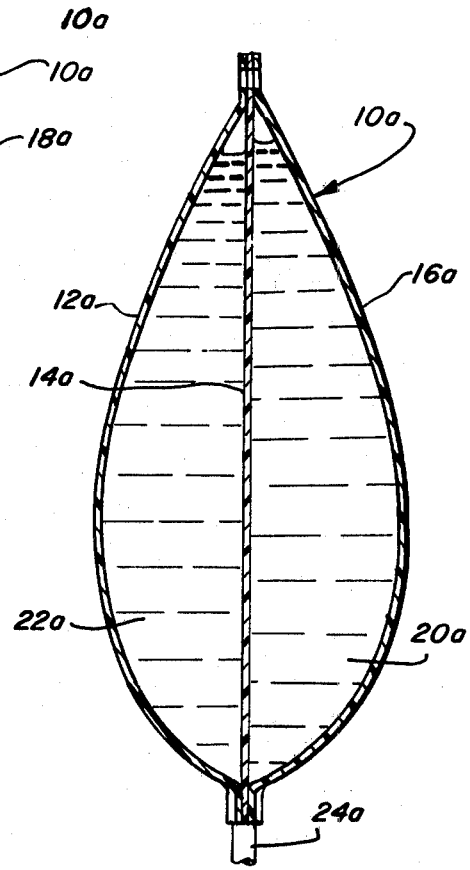
FIG. 6 is a longitudinal sectional view, taken along line 6—6 of FIG. 5, showing both chambers of the bag filled with peritoneal dialysis solution.

Referring to FIGS. 5 and 6, another embodiment of this invention using a similar bag is disclosed.

Solution bag 10a may be of similar construction to solution bag 10, with the exception that port tubes 24a, 26a join together in a Y connection to form a single connector tube 50, terminating in a connector 52 which may be of a design similar to that shown in U.S. Pat. No. 4,294,250.

As shown in FIG. 6, bag 10a carries three layers 12a, 14a, 16a sealed together at their peripheries in the manner of the previous embodiment. Port tubes 24a, 26a are similarly related in their connection through the sealed periphery 18a into the respective chambers 20a, 22a defined by bag 10a. A breakaway internal seal 30a may seal port tube 24a while, if desired, a slide clamp or other reclosable clamp 31a may seal port tube 26a.

As shown in FIG. 5, connector 52 may be in connecting relation with a connector 56. Connector 56 communicates with a peritoneal dialysis set 58 which may be of conventional design, having a connector member 60 on its end opposed from connector 56 communicating with peritoneal dialysis catheter 36a.

In use, peritoneal dialysis bag 10a is connected through its connector 52 to connector 56, taking the usual precaution to avoid contamination during the connection process. Clamp 31a may then be opened, along with slide clamp 57 (or the like) of set 58, to allow the spent peritoneal dialysis solution to flow from the peritoneal cavity through set 58 and port tube 26a into chamber 22a of bag 10a.

At the termination of this step, bag 10a can appear as it does in FIG. 6, with chamber 22a being filled with spent peritoneal dialysis and chamber 20a filled with fresh dialysis solution. Typically, the amount of fresh dialysis solution in chamber 20a is about two liters, while the amount of spent solution in chamber 22a may be somewhat more than that because of the water added to the solution by ultrafiltration. Bag 10a should, of course, be proportioned to permit it to hold the amount of liquid which it is expected to receive.

After draining of the peritoneal cavity, clamp 31a may be closed, and internal frangible seal 30a may be broken open to permit fresh peritoneal dialysis solution to flow through tubular port 24a, set 58, and implanted catheter 36a into the peritoneal cavity. After this has been accomplished, clamp 57 may be closed again and connectors 52, 56 separated. Connector 56 may be capped with a sealing cap member, and bag 10a, carrying the spent peritoneal dialysis solution, may be discarded.

One added advantage of this technique is that the outflow of spent peritoneal dialysis solution can take place immediately after the initial coupling between connectors 52, 56. This can tend to wash away any contamination that might have entered the system during the connection process, despite the efforts to keep the system sterile, so that the subsequent flow of fresh dialysis solution through connectors 52, 56 is less likely to wash contamination into the peritoneal cavity. Also, the connection may be sterilized with ultraviolet radiation or the like during the outflow or drain phase, so the connection is reliably sterilized prior to infusion of the fresh solution without any delay.

The above has been offered for illustrative purposes only, and is not intended to limit the scope of the invention, which is as defined in the claims below.

That which is claimed:

1. For use in peritoneal dialysis, a solution bag formed of three plastic walls sealed together about their peripheries to define a pair of separate chambers, port tubes communicating with each of said chambers, one of said chambers being filled with dialysis solution, said port tubes being joined together into a single tube, and connector means carried at an end of said single tube for connection with a mating connector on a conduit for communication with the peritoneal cavity of a patient, said bag having proportions capable of receiving an amount of spent dialysis solution in the other of said chambers generally similar in volume to the volume of dialysis solution in said one chamber prior to draining said one chamber, and means for releasably blocking flow through said port tubes.

2. A solution delivery system for peritoneal dialysis which comprises:
   a peritoneal tube for flow communication with the peritoneal cavity of a patient through one end thereof, said tube carrying a branched pair of tubular arms, one of said arms carrying a dialysis solution filter in flow communication therewith,
   solution bag means defining a pair of separate chambers, port tubes communicating with each of said chambers, one of said chambers being filled with dialysis solution and the other being empty, the port tube of said one chamber connecting with the tubular arm which carries the filter, and the port tube of the empty chamber connecting with the other tubular arm, and
   flow regulating means to control flow through said tubular arms, whereby fresh dialysis solution may pass from said one chamber through the filter and peritoneal tube, and spent dialysis solution may pass from the peritoneal tube through the other tubular arm into the other chamber without entering into contact with the filter.

3. The solution delivery system of claim 2 in which said solution bag means is a single bag formed of three plastic walls, sealed together about their periphery to define said pair of separate chambers.

4. The method of performing peritoneal dialysis, which comprises:
   establishing a sealed fluid flow path between the peritoneal cavity and a solution bag comprising a pair of separate chambers having port tubes communicating with each of said chambers and connecting together in a branched connection with a single conduit communicating with the peritoneal cavity, one chamber of said solution bag being filled with fresh peritoneal dialysis solution and the other chamber being empty; draining spent peritoneal dialysis solution from the peritoneal cavity to said empty chamber while the conduit communicating with the chamber having the fresh peritoneal dialysis solution is sealed; sealing the conduit communicating with the chamber containing the spent peritoneal dialysis solution; opening the conduit communicating with the chamber having fresh peritoneal dialysis solution to cause it to flow into the peritoneal cavity; and thereafter disconnecting said bag from communication with the peritoneal cavity.

5. The method of claim 4 in which said solution bag is formed of three plastic walls, sealed together about their periphery to define said pair of separate chambers.

6. The method of performing peritoneal dialysis, which comprises:
   establishing a sealed fluid flow path between the peritoneal cavity and solution bag means, said bag means comprising a pair of separate chambers having port tubes communicating with each of said chambers and connecting together in a branched connection with a single conduit communicating with the peritoneal cavity, one chamber of said solution bag means being filled with fresh peritoneal dialysis solution and the other chamber being empty;
   passing fresh peritoneal dialysis solution from said one chamber through a filter in one of the branched connections and through said single conduit into the peritoneal cavity;
   temporarily sealing the one branched connection carrying the filter at a position between the filter and the peritoneal cavity; and
   thereafter passing the peritoneal dialysis solution from the peritoneal cavity through the other of said branched connections into the other chamber of said solution bag, and disconnecting said bag from communication with the peritoneal cavity.

7. The method of claim 6 in which said solution bag means is a single bag formed of three plastic walls, sealed together about their periphery to define said pair of separate chambers.

8. The method of performing peritoneal dialysis which comprises:
   establishing sealed fluid flow paths between the peritoneal cavity and a solution bag, said bag comprising a pair of separate chambers having port tubes communicating with each of said chambers and connecting together in a branched connection with a single conduit communicating with the peritoneal cavity, one chamber of said solution bag being filled with fresh peritoneal dialysis solution the other chamber being empty;
   the branched connection which communicates with the filled chamber carrying a bacterial filter;
   sealing the branched connection carrying the filter at a position between the filter and the peritoneal cavity;
   passing spent peritoneal dialysis solution from the peritoneal cavity through the other of said branched connections into the other empty chamber of said solution bag;
   sealing said other branched connection and opening the one branched connection which has the filter; and
   thereafter passing fresh peritoneal dialysis solution from said one chamber through said filter into the peritoneal cavity, and disconnecting the bag from communication with the peritoneal cavity.

9. The method of claim 8 in which said solution bag is formed of three plastic walls, sealed together about their periphery to define said pair of separate chambers.

10. A solution delivery system for peritoneal dialysis which comprises:
- a peritoneal tube for flow communication with the peritoneal cavity of a patient through one end thereof, said tube carrying a branched pair of tubular arms;
- solution bag means defining a pair of separate chambers, ports communicating with each of said chambers, means for releasably connecting the port of each chamber respectively with one of said tubular arms;
- flow regulating means to separately control flow through said tubular arms; and
- access means positioned between said solution bag and flow regulating means to permit the introduction of sterilizing agent into one of said pair of tubular arms to sterilize the connecting means between the tubular arm receiving the sterilizing agent and the chamber port to which it is connected prior to passing dialysis solution therethrough.

11. The solution delivery system of claim 10 in which said access means is carried on one of said tubular arms, and the other of said tubular arms carries a dialysis solution filter in flow communication therewith, the other of said arms communicating with a bag chamber which carries fresh dialysis solution, while said one tubular arm communicates with an empty bag chamber.

12. The method of performing peritoneal dialysis, which comprises:
- establishing a sealed fluid flow path between the peritoneal cavity and a solution bag means, said bag means comprising a pair of separate chambers having port tubes communicating with each of said chambers and connected with a tubular set having a branched connection with a single conduit communicating with the peritoneal cavity;
- inserting antiseptic into one of said branched connections while sealing said branched connection at a position more remote from the bag than the point of said insertion, to allow said antiseptic to sterilize the connection between said tubular set and the port tube;
- passing peritoneal dialysis solution from the peritoneal cavity through said one branched connection into a chamber of said solution bag, thereby washing the antiseptic into said solution bag; and
- thereafter passing fresh peritoneal dialysis solution from the other chamber through the other of said branched connections and through said single conduit into the peritoneal cavity.

13. The method of claim 12 in which said other branched connection carries a filter.

14. The method of claim 12 in which said antiseptic is povidone iodine.

* * * * *